(12) United States Patent
Tonks

(10) Patent No.: US 7,699,973 B2
(45) Date of Patent: Apr. 20, 2010

(54) RAPID ANALYTE MEASUREMENT ASSAY

(75) Inventor: Simon Tonks, Abingdon (GB)

(73) Assignee: Abbott Diabetes Care Inc., Alameda, CA (US)

( * ) Notice: Subject to any disclaimer, the term of this patent is extended or adjusted under 35 U.S.C. 154(b) by 388 days.

(21) Appl. No.: 11/479,544

(22) Filed: Jun. 30, 2006

(65) Prior Publication Data

US 2008/0000780 A1    Jan. 3, 2008

(51) Int. Cl.
    *G01N 27/327*    (2006.01)
(52) U.S. Cl. .............................. 205/777.5; 204/403.01; 204/406
(58) Field of Classification Search ............ 204/403.01, 204/403.02, 403.04, 403.14, 406; 205/777.5, 205/792
    See application file for complete search history.

(56) References Cited

U.S. PATENT DOCUMENTS

| | | | |
|---|---|---|---|
| 4,085,009 A | 4/1978 | Pace |
| 4,260,680 A | 4/1981 | Muramatsu et al. |
| 4,897,162 A | 1/1990 | Lewandowski et al. |
| 5,262,305 A | 11/1993 | Heller et al. |
| 5,264,104 A | 11/1993 | Gregg et al. |
| 5,320,725 A | 6/1994 | Gregg et al. |
| 5,356,786 A | 10/1994 | Heller et al. |
| 5,593,852 A | 1/1997 | Heller et al. |
| 5,628,890 A | 5/1997 | Carter et al. |
| 5,665,222 A | 9/1997 | Heller et al. |
| 5,820,551 A | 10/1998 | Hill et al. |
| 5,972,199 A | 10/1999 | Heller et al. |
| 6,071,699 A | 6/2000 | Meade et al. |
| 6,103,033 A | 8/2000 | Say et al. |
| 6,120,676 A | 9/2000 | Heller et al. |
| 6,129,823 A | 10/2000 | Hughes et al. |
| 6,134,461 A | 10/2000 | Say et al. |
| 6,143,164 A | 11/2000 | Heller et al. |
| 6,175,752 B1 | 1/2001 | Say et al. |
| 6,241,863 B1 * | 6/2001 | Monbouquette ......... 205/777.5 |
| 6,251,260 B1 | 6/2001 | Heller et al. |
| 6,294,062 B1 * | 9/2001 | Buck et al. .................. 204/400 |
| 6,338,790 B1 | 1/2002 | Feldman et al. |
| 6,340,597 B1 * | 1/2002 | Svorc et al. .............. 204/403.1 |
| 6,503,381 B1 | 1/2003 | Gotoh et al. |
| 6,551,494 B1 | 4/2003 | Heller et al. |
| 6,592,745 B1 | 7/2003 | Feldman et al. |
| 6,746,582 B2 | 6/2004 | Heller et al. |
| 6,773,671 B1 | 8/2004 | Lewis et al. |
| 6,863,800 B2 | 3/2005 | Karinka et al. |

(Continued)

FOREIGN PATENT DOCUMENTS

WO    WO 2005/003774 A1 *    1/2005

OTHER PUBLICATIONS

Pinter et al, Meeting Abstract, 227th ACS National Meeting, 2004.*

(Continued)

*Primary Examiner*—Kaj K Olsen
(74) *Attorney, Agent, or Firm*—Edward J. Baba; Bozicevic, Field & Francis LLC

(57) ABSTRACT

The present the invention provides methods, devices and systems for rapidly measuring analytes within a biological sample.

17 Claims, 9 Drawing Sheets

U.S. PATENT DOCUMENTS

| | | |
|---|---|---|
| 7,045,310 B2 | 5/2006 | Buck, Jr. et al. |
| 7,049,068 B2 | 5/2006 | Thorp et al. |
| 2003/0159945 A1 | 8/2003 | Miyazaki et al. |
| 2003/0178322 A1* | 9/2003 | Iyengar et al. ............... 205/775 |
| 2006/0113187 A1* | 6/2006 | Deng et al. ............ 204/403.01 |
| 2008/0083618 A1* | 4/2008 | Neel et al. ............. 204/403.14 |

OTHER PUBLICATIONS

Bard and Faulkner, Electrochemical Methods, 2nd Ed., 2001, pp. 293-299.*

Biosensors & Bioelectronics 17 (2002), pp. 441-456.*

* cited by examiner

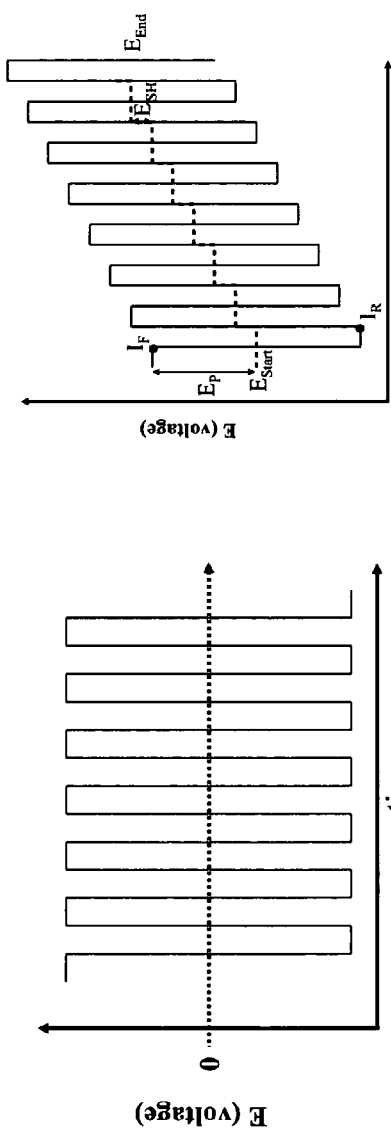
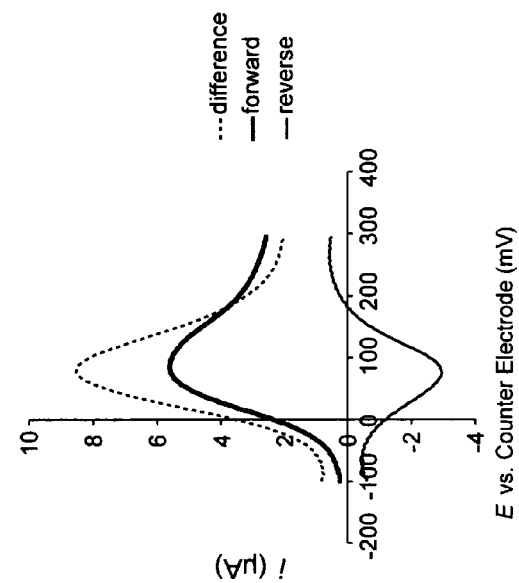
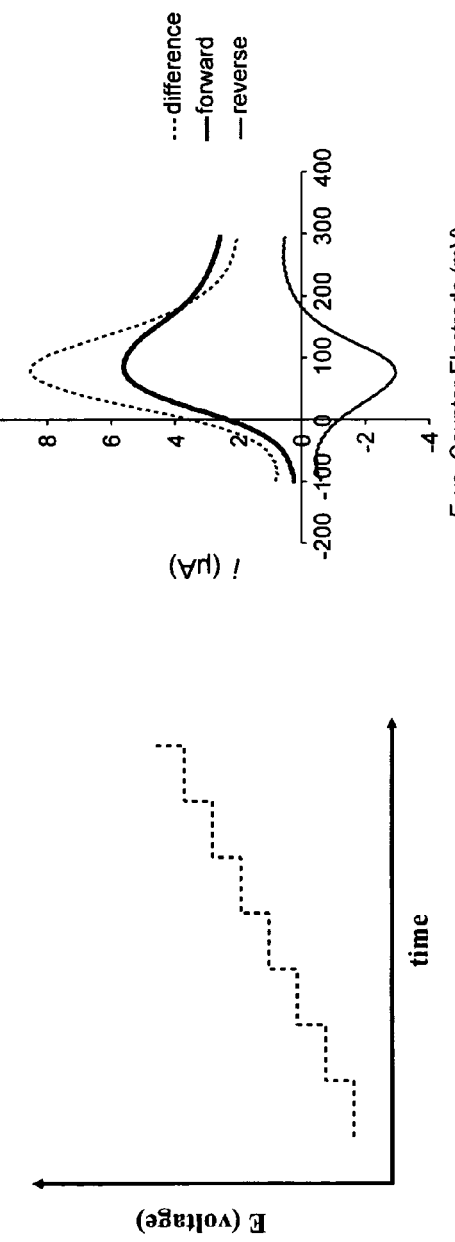
FIG. 1A
FIG. 1B
FIG. 1C
FIG. 1D 15 mM 15 mM

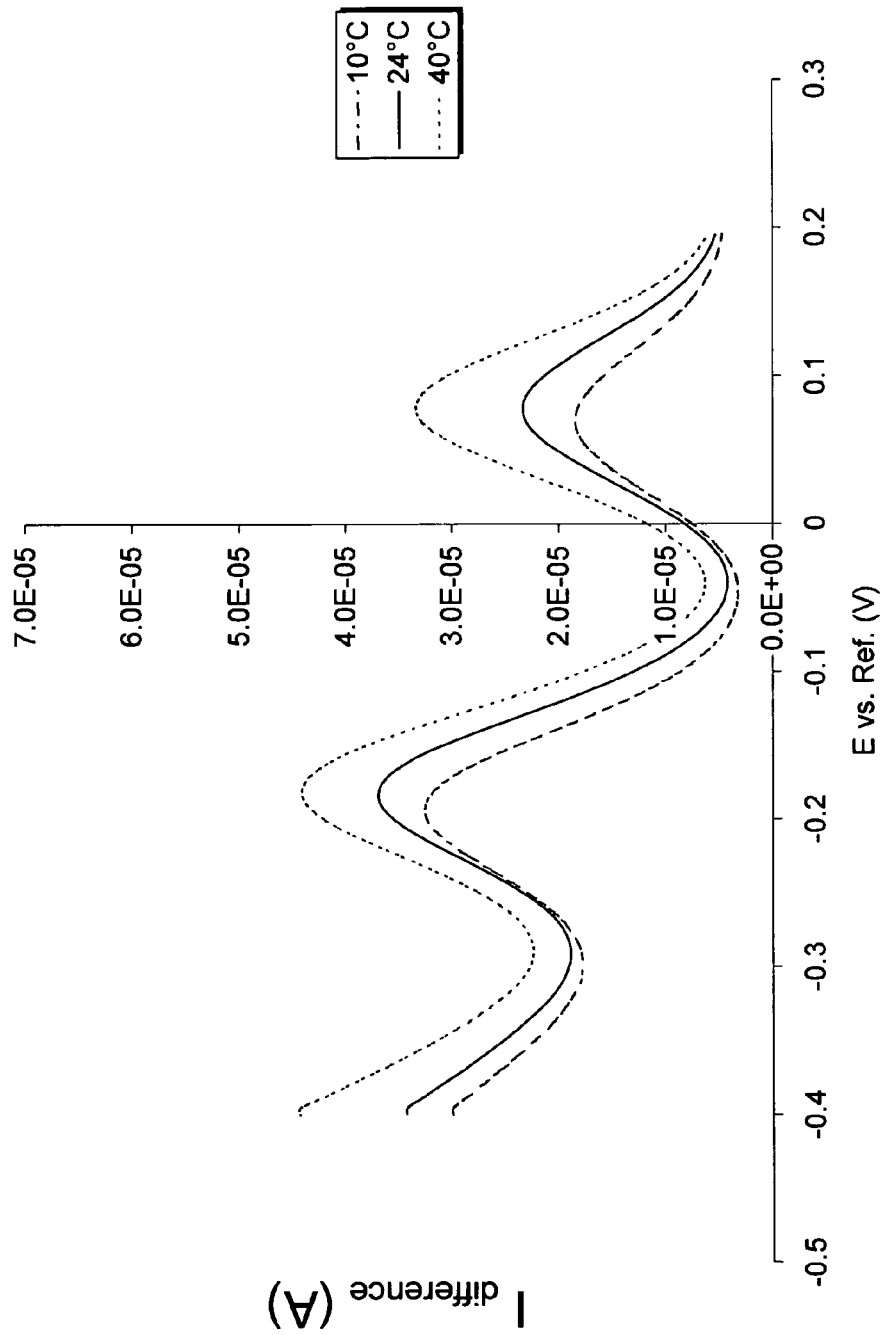

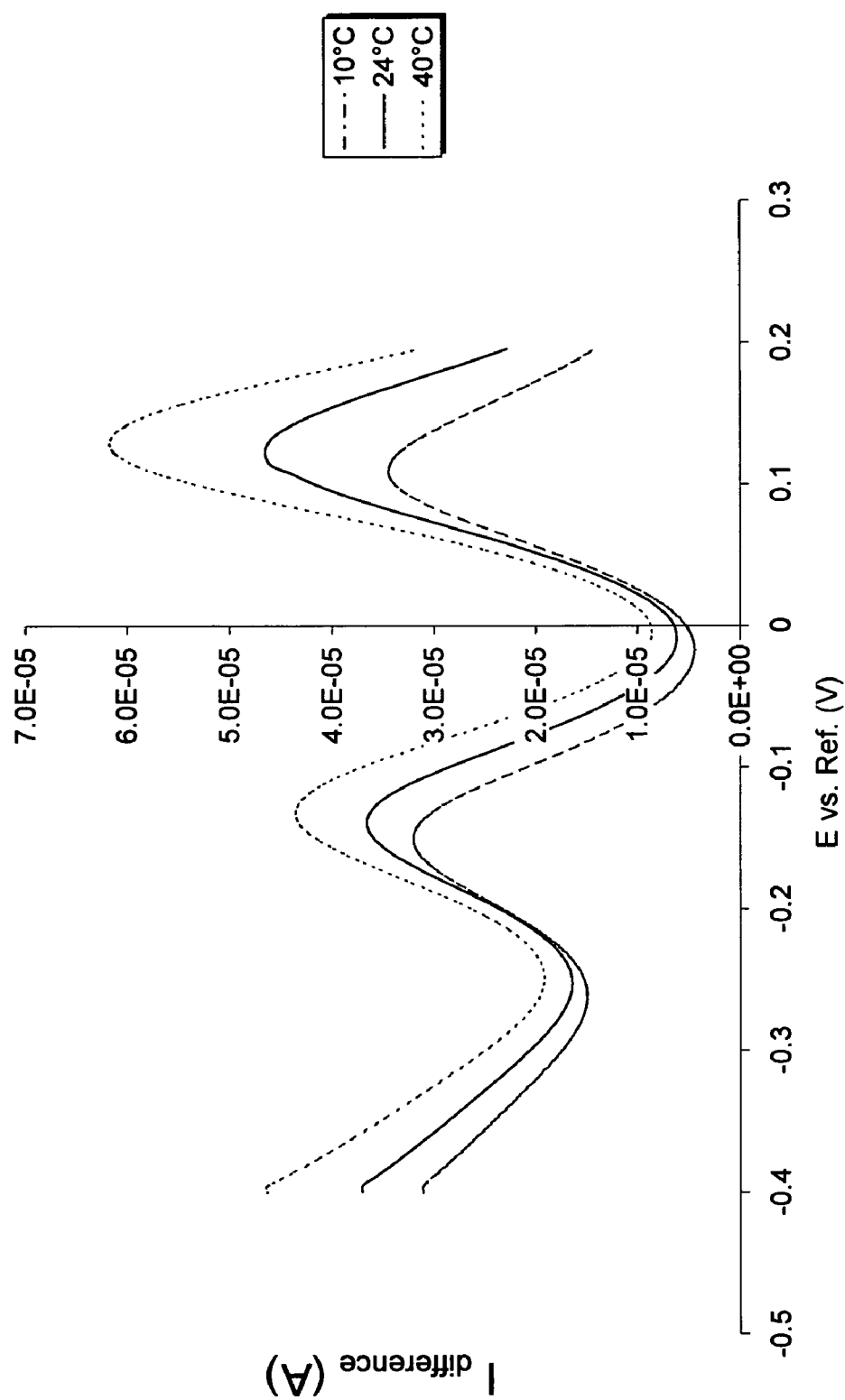

RAPID ANALYTE MEASUREMENT ASSAY

FIELD OF THE INVENTION

The present invention is related to methodologies for the detection of analytes in biological samples.

BACKGROUND

Analyte concentration determination in biological fluids is of ever increasing importance. Such assays find use in a variety of applications and settings, including clinical laboratory testing, home testing, etc., where the results of such testing play a prominent role in the diagnosis and management of a variety of disease conditions. Common analytes of interest include glucose for diabetes management, cholesterol for monitoring cardiovascular conditions, and creatinine, creatine, urea and the like. In response to this growing importance of analyte concentration detection, a variety of analyte detection protocols and devices for both clinical and home use have been developed.

One type of method that is employed for analyte detection is an electro-chemical-based method. In such methods, a sample of a substance to be tested, e.g., a biological substance typically in aqueous liquid form, e.g., blood, is placed into a reaction zone in an electrochemical cell made up of at least two electrodes, i.e., a counter/reference electrode and a working electrode. Most electrochemical biosensors employ one of three conventional methodologies: coulometry (measuring charge), chronoamperometry (measuring current), and chronopotentiometry (measuring potential or voltage). In coulometry and chronoamperometry, typically, a redox reagent system is present within the reaction zone. Such a reagent system includes one or more enzymes and a mediator. The enzyme usually functions to oxidize the analyte of interest. When the sample is deposited into the electrochemical cell, the targeted analyte comes into contact with the enzyme(s) and reacts therewith forming reduced enzyme. The mediator in turn reacts with and regenerates the oxidized form of the enzyme, itself being reduced. The reduced mediator is then oxidized at the working electrode. The resultant charge or current generated by such a reaction is measured. The magnitude of the measured charge or current is proportional to the concentration of the target analyte present in the biological substance being tested.

The above-described electrochemical cell is commonly used in the form of a disposable test strip on which the biological sample is deposited and which is receivable within a meter by which the analyte concentration is determined. Examples of assay systems that employ these types of test strips, often referred to as biosensors, and meters may be found in U.S. Pat. Nos. 6,129,823, 6,773,671, 6,143,164, 6,592,745, 6,338,790, 6,503,381, 5,628,890, 5,820,551, 6,251,260, 6,551,494, 6,863,800, and U.S. patent application Ser. No. 11/147,532.

For successful commercialization as a consumer product, user convenience is key. The less intrusive the testing activity, the more likely patients will comply with required testing regime and the better their medical conditions are able to be managed. One way of minimizing the intrusiveness of analyte measurements is to provide rapid assays.

However, the presence of hematocrit, i.e., red blood cells, within the blood may affect the accuracy of measuring a targeted analyte, e.g., glucose, using rapid assay biosensors for use with whole blood samples. This is so as hematocrit tends to change the rate of diffusion of species within the blood sample or otherwise hinder the performance of the test. The sensitivity to hematocrit level is generally exaggerated with shorter assay times. Accordingly, the presence of hematocrit represents a significant challenge to the development of short assay systems for the measurement of blood analytes. While there are conventional systems that afford relatively short assays which also perform a secondary assay that estimates hematocrit level for the purpose of signal compensation; such secondary assay adds to the overall assay time, presenting a significant drawback.

Conventional electrochemical detection techniques have other drawbacks as well, particularly with respect to the measurement of blood analytes. Because sensors employing single potential step techniques are not capable of decoupling multiple signals, those configured to determine glucose concentration in blood may be susceptible to influence from other interfering substances that may be present in the sample and oxidized at voltages similar to, or lower than that required for oxidation of the chosen mediator. As such, any of these interfering substances may be mistakenly identified as the analyte of interest—for example glucose in certain systems. These effects will give artificially elevated estimates of the analyte concentration. Additionally, conventional analyte detection systems are typically capable of, or limited to measuring only a single analyte.

Environmental factors such as temperature and humidity, that can influence sample temperature and evaporation, may also have an effect the accuracy of analyte measurements. Most prior art analyte measurement systems rely solely on simple electronic components (such as a thermistor embedded in a meter) to compensate for errors that might arise due to temperature. Relative to the rapid temperature equilibration of a small sample drop, thermistors are relatively slow in sensing changes in temperature. See, for example, U.S. Patent Application Publication No. 2003/0159945. This is particularly important where the meter may be used shortly after being moved from a relatively warm place to a relatively cooler one or visa versa. In this case, an incorrect temperature compensation factor may be applied to the test result. Some manufacturers have gone to some length to address the influences of temperature in analyte measurements by adding additional components, e.g., secondary thermistors, and more complex circuitry in an attempt to prevent such errors. Such electronic hardware increases costs and space requirements of an analyte measurement meter.

Accordingly, it is desirable to develop an easy to use analyte sensor capable of performing a rapid yet accurate assay to determine the concentration of one or more analytes from a single blood sample, independent of the blood hematocrit level and environmental conditions at the time of testing. Such a sensor would be particularly useful and beneficial for blood analyte measurements such as glucose concentration.

SUMMARY OF THE INVENTION

The present invention includes devices, systems and methods for the rapid assay of analytes in small-volume samples. In one aspect, the invention includes the use of square wave voltammetry (SWV) to measure the concentration of one or more target analytes. Whilst commercially available blood glucose diagnostic systems based on conventional methodologies have assays that typically complete in the order of several seconds, SWV assays of the subject invention may complete in shorter time frames, e.g., less than about one second, i.e., from the user's perspective, the assay is virtually instantaneous.

Another aspect of the invention is the ability to compensate for influences from factors which may interfere with the assay process and thus result in an inaccurate measurement. As discussed above, with conventional systems, the sensitivity to interferences such as hematocrit is particularly marked at short assay times. The inventor found this also to be true of hematocrit sensitivity when SWV methodology was employed in conjunction with a typical active chemistry system, i.e., enzyme and mediator. The present invention circumvents this issue via the incorporation of one or more secondary redox couples (in addition, in known quantity, to the primary redox couple selected to mediate with the targeted analyte) within the reaction area of the electrochemical cell which do not mediate with the targeted analyte, as internal controls. As a potential scanning technique, SWV methodology may also be used to decouple electroactive interfering species in the test sample.

Environmental factors that have an effect on the sample, e.g., temperature, may also be compensated for by the use of a second redox couple that acts as an internal standard or control. Conventional systems that rely on electrical components within a meter to indirectly estimate sample temperature cannot guarantee the same degree of accuracy. As such, the present invention provides a level of accuracy in the measurement of analytes that is not achievable within the same timeframe using conventional techniques.

In one variation of the invention, SWV is used to rapidly measure the concentration of glucose in very small volumes of blood applied to an electrochemical cell, where the assay parameters are configured to reduce the time in which the assay is performed and/or to compensate for certain interfering factors including but not limited to the presence of hematocrit within the blood sample and/or the sample's temperature. In certain embodiments, this technique is used to measure glucose concentrations in blood samples having a volume of about 1 µL or less, e.g., about 0.6 µL or less, e.g., 0.3 µL or less, and within less than about 1 second. This methodology allows single measurements to be made in tenths of a second, or less.

The subject systems include biosensors (or sensors) configured for measuring analytes applied to an electrochemical cell using the SWV methodology. The systems include a meter configured to execute square wave voltammetry. The subject devices include electrochemical cells provided in disposable test strip form or any other practical form which contain one or more redox couple(s) particularly selected for mediation efficiency with enzyme reaction products resultant from reaction with the target analyte (referred to herein as "primary redox couples"), and one or more additional redox couples that are target analyte independent, and do not interact/react with the primary redox couple (referred to herein as "secondary redox couples").

In one application, a subject system is configured to measure glucose concentration in blood. In certain embodiments, the system includes a meter configured to analyze a very small sample of blood according the SWV methodology, where the sample is applied to an electrochemical cell containing a redox reagent system having a primary redox couple selected for its ability to mediate with products of an enzyme/glucose reaction as well as an additional or secondary redox couple that generates a glucose concentration and primary redox couple concentration independent signal. The secondary redox couple is selected to have an oxidation potential set sufficiently far apart from that of the primary redox couple, i.e., the mediator, such that their signals may be decoupled, but in many embodiments not so far apart that it adversely affects the assay time. The secondary redox couple acts as an internal standard, the signal from which is similarly (to the primary redox couple) impacted by changes in the physical properties sample, such as temperature and hematocrit (which may be considered as a diffusion rate modifier). Deviations in the magnitude of the secondary redox couple (internal standard) from an expected value are used to correct the glucose concentration calculated from the measured primary mediator signal.

These and other features, objects and advantages of the invention will become apparent to those persons skilled in the art upon reading the details of the invention as more fully described below.

BRIEF DESCRIPTION OF THE DRAWINGS

The invention is best understood from the following detailed description when read in conjunction with the accompanying schematic drawings. To facilitate understanding, the same reference numerals have been used (where practical) to designate similar elements that are common to the drawings. Included in the drawings are the following:

FIG. 1A shows a square wave voltage.

FIG. 1B shows a voltage potential step (staircase) function.

FIG. 1C shows the square wave voltammetry excitation signal, i.e., a square wave signal (FIG. 1A) superimposed on a voltage step (ramp) function (FIG. 1B), that is applied to an electrochemical cell for analyte measurements according to the methodology of the present invention.

FIG. 1D is a plot showing the current outputs sampled towards the end of each forward ($I_F$) and reverse ($I_R$) square wave pulse, and the difference current ($I_D$), generated by an electrochemical cell in which a single redox couple is present to which a voltage signal of the form illustrated in FIG. 1C has been applied.

FIGS. 8A and 8B are graphs showing the effect of temperature on a sample of fixed glucose concentration (at 3 mM and 15 mM) applied to electrochemical cells having a glucose-dependent mediator and a glucose-independent redox couple.

Figure 2:
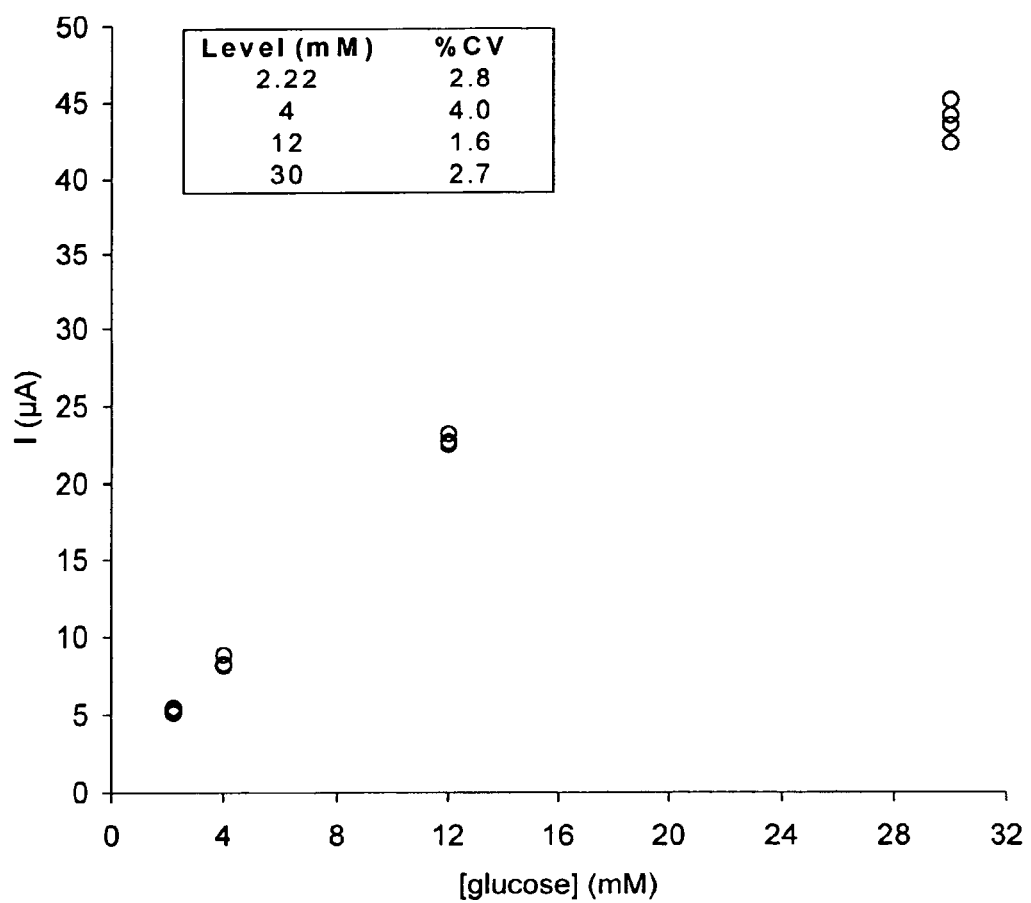
FIG. 2 is a graph of mediator peak current (I) as a function of the concentration of glucose when aqueous glucose solutions are applied to an electrochemical cell containing glucose dependent enzyme and mediator to which a voltage waveform having the characteristics of the signal depicted in FIG. 1C is applied according to the methodology of the present invention.

Variation of the invention from that shown in the figures is contemplated.

DETAILED DESCRIPTION OF THE INVENTION

While the details of the present invention are described and illustrated in the context of measuring glucose concentration in a blood sample, such application is not intended to be limiting but merely exemplary of the present invention.

As mentioned above, embodiments of the present invention include the use of SWV methodology to reduce the measurement time for determining the concentration of glucose in volumes, e.g., small volumes, of blood applied to an electrochemical cell. In particular, a devices, systems and method of embodiments of the present invention involve the application of a potential waveform to an electrochemical cell configured for glucose concentration determination, wherein certain embodiments the applied potential waveform includes a square wave (see FIG. 1A) superimposed on top of a potential step function (see FIG. 1B). The resulting potential waveform is shown in FIG. 1C, where $E_P$ is the magnitude of the cathodic and anodic potential pulses away from the staircase potential steps, and $E_{SH}$ is the magnitude of each potential step. The exemplary resulting current response (I) of the electrochemical cell, illustrated in FIG. 1D, varies proportionally with the concentration of glucose in the sample contained within the cell. The response is amplified as a difference between the forward ($I_F$) and reverse ($I_R$) currents (i.e., the oxidizing and reducing currents) measured during the course of the detection period. It should also be noted that the integrated charge under the peak, rather than peak current, may also be correlated to analyte, in this case glucose, concentration.

The assay time, i.e., the time in which a viable measurement of the output current can be made, is a function of the potential range being scanned (the difference between the applied voltage at the end ($E_{End}$), and the applied voltage at the start ($E_{Start}$) of the measurement period), the staircase potential step height ($E_{SH}$), and the frequency at which the staircase potential is stepped (f), in accordance with the following equation:

$$\text{Assay Time} = \frac{(E_{End} - E_{Start}) \cdot f}{E_{SH}}$$

Typically, the voltage range scanned is in the order of about 1 volt, and the voltage is stepped across this range at a relatively high frequency (f), i.e., in the order of hundreds to thousands of Hz, which makes for a very short assay time. By way of an example, if the voltage range scanned is 800 mV, stepping the voltage in 10 mV steps, at a frequency of 100 Hz, the assay is complete in 0.8 seconds.

Experimentation validating the methodologies of the present invention is now described. It is understood that the following experimental examples are put forth so as to provide those of ordinary skill in the art with a complete disclosure and description of how to make and use the present invention, and are not intended to limit the scope of what is regarded as the invention nor are they the only experiments performed. Efforts have been made to ensure accuracy with respect to numbers used (e.g., amounts, temperature, etc.) but some experimental errors and deviations should be accounted for. Unless indicated otherwise, glucose concentrations are quoted in millimolar (mM), hematocrit as % Hct, and temperature is reported in degrees Centigrade.

The methodology was first evaluated using test sample of aqueous solutions containing known concentrations of glucose (2.22 mM, 4 mM, 12 mM and 20 mM, respectively) applied to test strips containing only a glucose-specific enzyme and mediator (without any secondary redox couples) in order to verify that a glucose response was obtainable by SWV. The electrochemical test strips were configured with three electrodes—working, counter and reference electrodes. A square wave voltammetry signal, as illustrated in FIG. 1C, set to scan across an appropriate voltage range was applied to the test strips using a potentiostat. The resultant currents (described above) were recorded with the peak difference currents plotted as a function of glucose concentration, as illustrated in the graph of FIG. 2. The graph shows the expected linear relationship between output current and glucose concentration. Specifically, the current output increases with greater concentrations of glucose. It was found that glucose responses could also be obtained with the system configured with only two electrodes, i.e., a working electrode and a combined counter/reference electrode, and/or by integrating the area under the peak and correlating the measured charge to glucose concentration.

Figure 3:
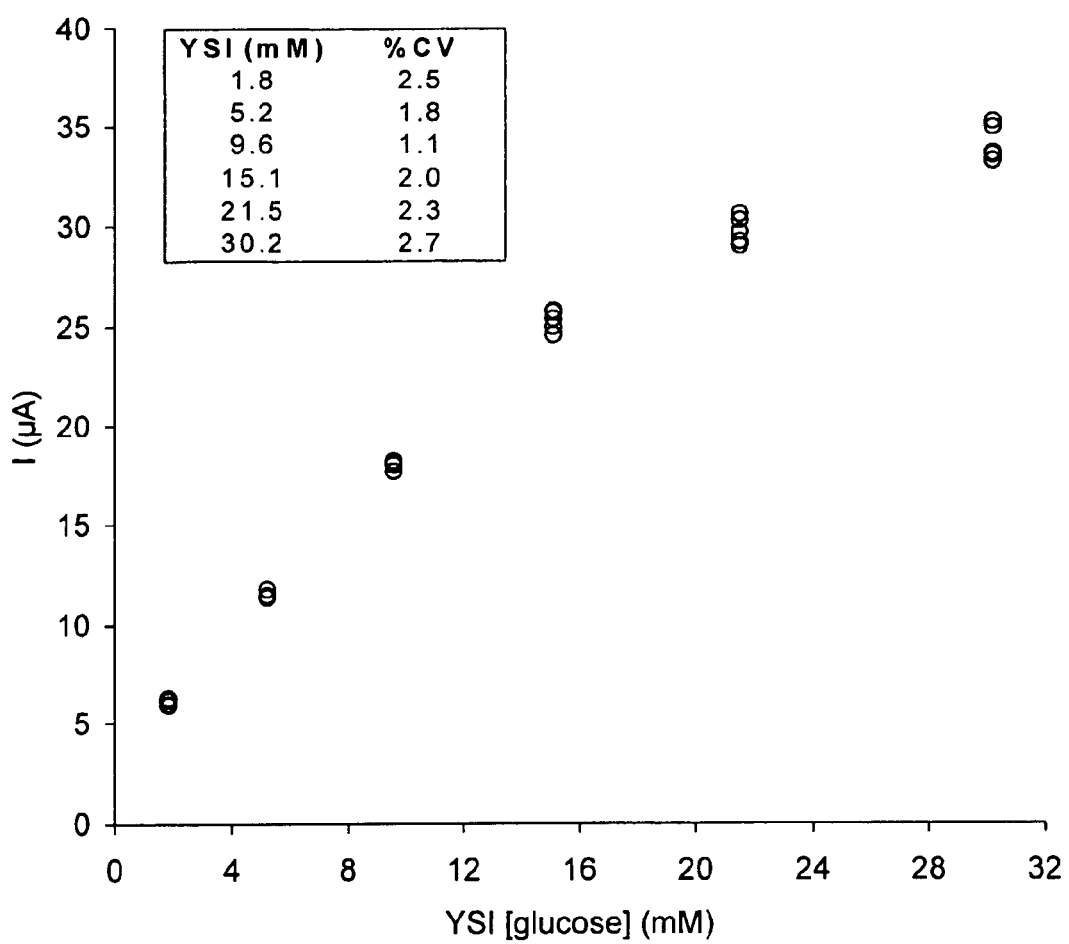
FIG. 3 is a graph of mediator peak current (I) as a function of the concentration of glucose in samples of venous blood spiked with glucose upon application to an electrochemical cell containing glucose dependent enzyme and mediator to which a voltage waveform having the characteristics of the signal depicted in FIG. 1C is applied according to the methodology of the present invention.

Having determined that the subject methodology produces expected results with the aqueous solutions, the same methodology was then evaluated with venous blood spiked with known concentrations of glucose (1.8 mM, 5.2 mM, 9.6 mM, 15.1 mM, 21.5 mM and 30.2 mM, respectively). The peak difference currents achieved upon application of a square wave voltammetry signal, as illustrated in FIG. 1C, to test strips to which the spiked venous blood was applied are plotted as a function of glucose concentration in the graph of FIG. 3. The graph again shows a substantially linear relationship between output current and glucose concentration in blood. The inventor found this relationship to be more linear when integrated current data was used in place of peak current data as a measure of glucose concentration.

Figure 4A:
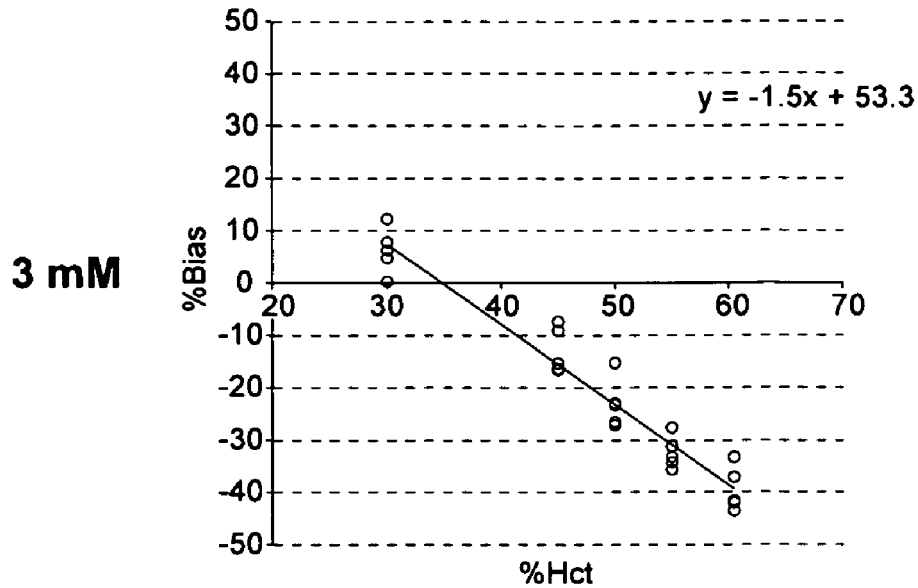
FIGS. 4A and 4B are graphs illustrating the bias introduced in the uncompensated SWV glucose measurement by variance in hematocrit level in the blood samples at glucose concentrations of 3 mM and 15 mM, respectively.
Figure 4B:
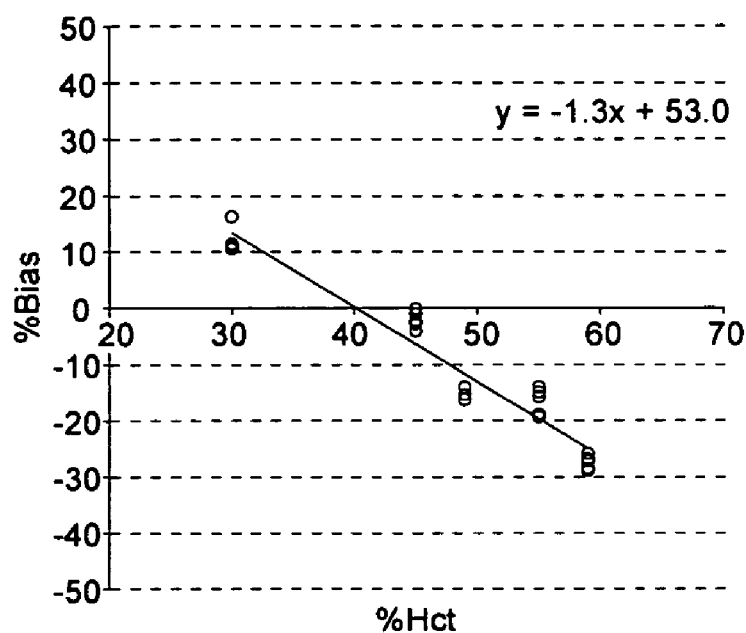

As mentioned above, changes/variation in the physical properties of the sample may affect the accuracy of the measurement of a targeted analyte. It is known that hematocrit levels in blood have a significant effect on electrochemical-based measurements of glucose; the effect is typically magnified in rapid assays. See, for example, U.S. Patent Application Publication No. 2003/0159945. In order to determine whether such hematocrit effect was present with the subject SWV methodology of the of the present invention, experiments were conducted using venous blood samples spiked with a known concentration of glucose (either 3 mM or 15 mM) but adjusted to have known but varying concentrations of hematocrit (% Hct). The effect of hematocrit level is shown in the graphs of FIGS. 4A and 4B at known, fixed glucose concentrations of 3 mM and 15 mM, respectively. As can be seen by the biases shown in FIGS. 4A and 4B, hematocrit levels do affect 'classical' SWV methodology's ability to accurately measure glucose concentrations in blood.

Figure 5A:
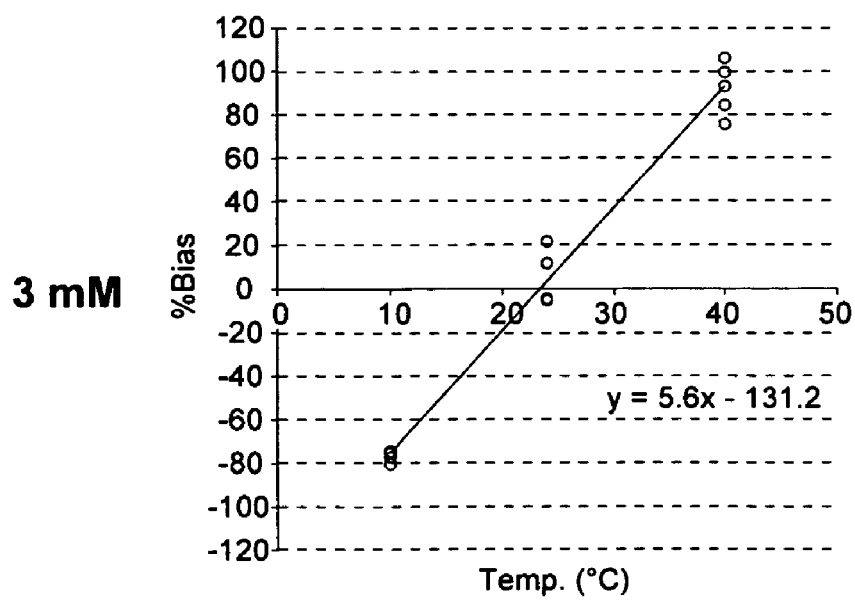
FIGS. 5A and 5B are graphs illustrating the effect of sample temperature on the uncompensated SWV measured glucose concentrations in blood samples having known glucose concentrations of 3 mM and 15 mM, respectively.
Figure 5B:
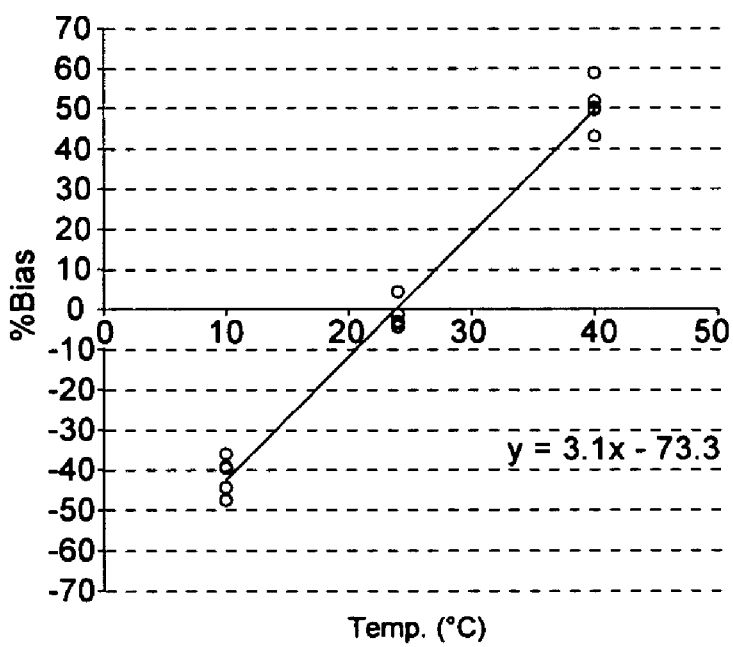

Also, as mentioned above, sample temperature may affect the accuracy of the measurement of a targeted analyte. The effect of temperature on a 'classical' SWV glucose measurement is plotted in the graphs of FIGS. 5A and 5B for the known glucose concentrations of 3 mM and 15 mM, respectively. As the graphs illustrate, temperature also has a significant effect on the ability of a system to accurately the glucose concentration in a test sample.

Since the charge transfer reaction and diffusion rate of a secondary redox couple is similarly (to the primary redox couple) effected by temperature and changes in the physical properties of the sample, e.g. hematocrit, the secondary redox couple in known quantity would provide a current response that could be used to compensate measurement results of the target analyte for unwanted effects such as sample temperature and hematocrit. It may also be possible to measure glucose independent of the sample media, e.g. whole blood versus control test solutions.

To validate such findings, experimentation was conducted with the SWV methodology of the present invention using electrochemical cell redox reaction systems including a glucose-dependent mediator along with an appropriate glucose-independent redox couple. Those skilled in the art will recognize that the choice of secondary couple is highly dependent upon the enzyme and primary redox couple that is the mediator.

In certain embodiments, the secondary redox couple is incorporated within the active reagents in electrochemical cell on board the test strip.

Venous blood samples with a fixed hematocrit level and spiked with known concentrations of glucose (2.5 mM, 5 mM, 10 mM, 15 mM, 20 mM, 27 mM and 35 mM, respectively) were applied to test strips that included a fixed amount of secondary redox couple. The SWV excitation signal of FIG. 1C was then applied to the test strips with the various response currents shown in the graph of FIG. 6. It is clear that unlike the primary redox couple, i.e. the mediator, the magnitude of the secondary redox couple is independent of glucose concentration.

A similar process was performed with samples of spiked venous blood having a fixed glucose concentration (15 mM) but adjusted hematocrit levels (20%, 30%, 42%, 53% and 66%, respectively). As seen from the graph of FIG. 7, the resulting current peaks for each sample indicate that the diffusion rates for both glucose dependent and glucose independent redox couples are similarly effected by changes in hematocrit level. As such, the glucose measurements may be corrected by a factor calculated based on the sign and magnitude of % bias of the secondary redox couple's measured response versus it's expected response.

$$[glucose]_{actual}=[glucose]_{measured}*\% \text{ bias of secondary signal from expected}*-1*\text{correction factor}$$

where the correction factor may be derived empirically for a particular active chemistry formulation that includes the secondary redox couple.

Next, a variation in the above experiment was made to assess the effect of sample temperature (10, 24 and 40° C.) on the secondary redox couple and the primary glucose responses at a fixed glucose concentration (3 mM). As seen from the graphs in FIGS. 8A and 8B, the resulting current peaks indicate that the reaction kinetics for both glucose dependent and glucose independent redox couples are effected by changes in sample temperature. As such, the effect of sample temperature on glucose measurements may be corrected by a factor calculated based on the sign and magnitude of % bias of the secondary redox couple's measured response versus it's expected response.

$$[glucose]_{actual}=[glucose]_{measured}*\% \text{ bias of secondary signal from expected}*-1*\text{correction factor}$$

where the correction factor may be derived empirically for a particular active chemistry formulation that includes the secondary redox couple.

Figure 6:
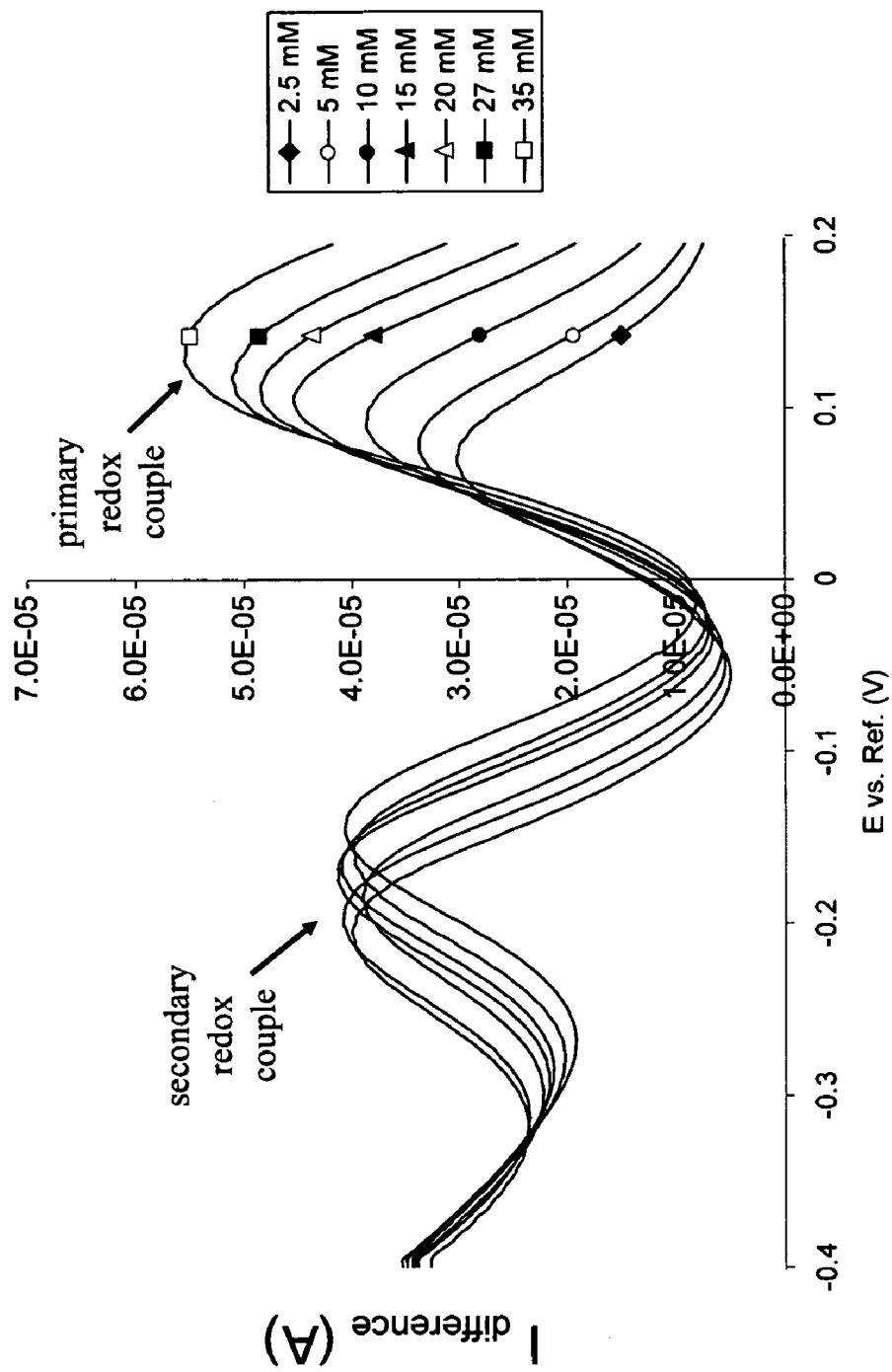
FIG. 6 shows the SWV response of a system, to a series of samples with glucose concentrations ranging from 2.5 to 35 mM, in which both a primary redox couple (mediator) and secondary (glucose independent) redox couple are present.
Figure 7:
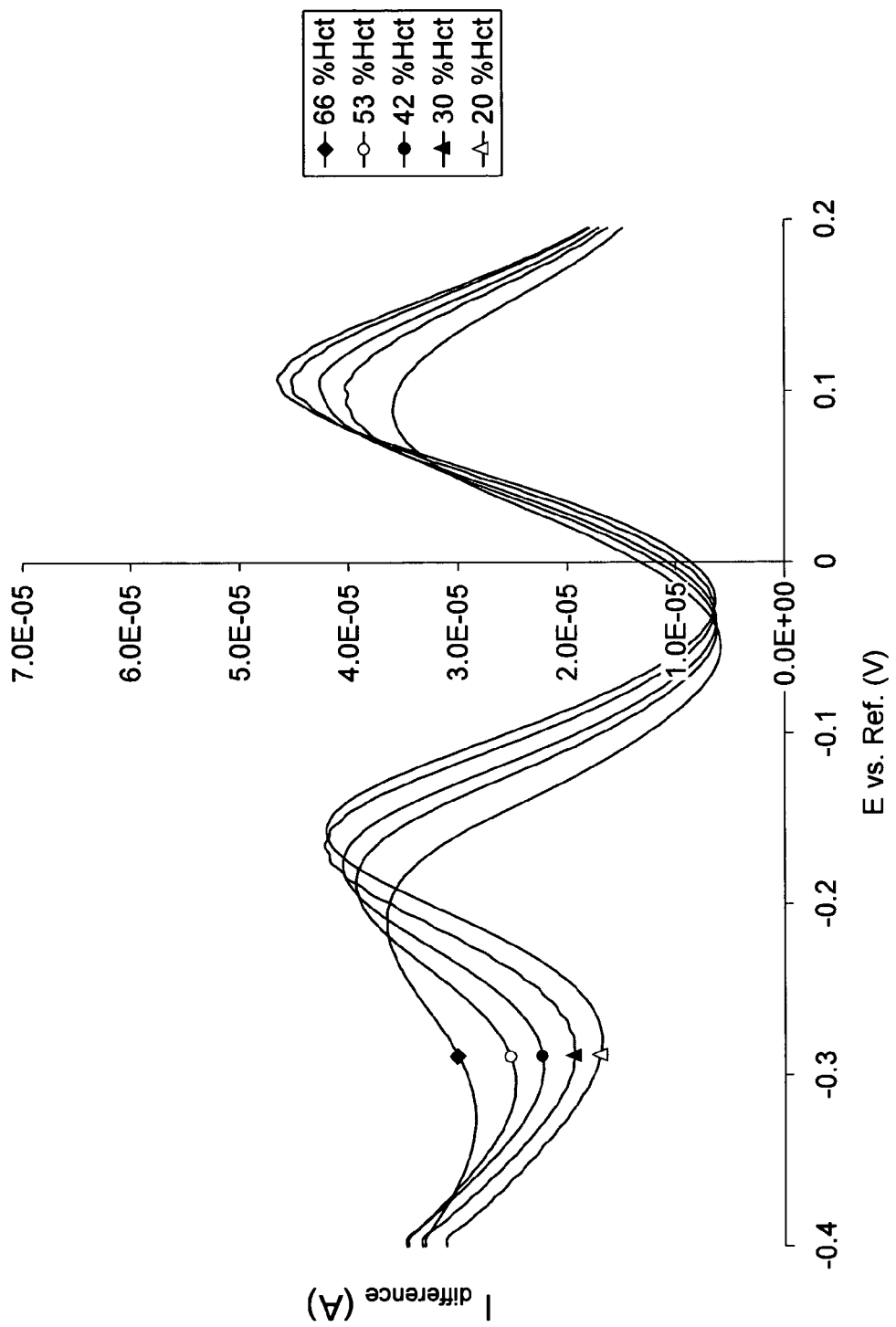
FIG. 7 is a graph showing the effect of hematocrit level (at a fixed glucose level, 15 mM) within blood samples applied to electrochemical cells having a glucose-dependent mediator and a glucose-independent secondary redox couple.

As illustrated in the graphs of FIGS. 6 to 8, the secondary redox couple has been selected such that its half-wave potential is sufficiently different from that of the glucose mediator so that the two signals may be decoupled. In one approach, the peak responses of the respective mediating and non-mediating redox couples have minimal if no overlap. However, overlapping peaks may be decoupled with post signal processing. At the same time, so as not to adversely affect the overall assay time, the secondary redox couple is selected such that its half-wave potential is not significantly separated from that of the mediator component, i.e. so as to curtail the scan range.

Also provided by the present invention are devices and/or systems configured for carrying out the subject methodology. For example devices include meters configured for applying the requisite voltage signals to an electrochemical cell containing a sample fluid, measuring the current response of the cell and, based on this current response, determining the concentration of a target analyte. More particularly, the meter includes means for generating and applying a SWV signal to the electrochemical cell and hardware and software for employing algorithms to calculate the concentration of the target analyte in the sample applied to the cell, and applying a correction factor to the measured concentration to compensate for variations in the physical properties of the sample. The devices also include test strips having electrochemical cells for receipt of a small-volume biological sample, where the test strip is configured for electrical engagement with a meter. The electrochemical cell and the means for signal application, detection and measurement may be integrated into a biosensor (or sensor). The subject systems include a meter and test strips or an integrated biosensor or the like.

The methods of the present invention may be performed using the subject devices and systems or by other means. The methods may all comprise the act of providing a suitable voltage source, voltage, electrochemical cell, test strip, meter, device, system, etc. Such provision may be performed by the end user. In other words, the act of "providing" merely requires the end user obtain, access, approach, position, set-up, activate, power-up or otherwise act to provide the requisite object used in the subject method. Likewise, the various acts of mechanical and/or electrical actuation are included in some of the subject methods.

Yet another aspect of the invention includes kits having any combination of devices described herein—whether provided in packaged combination or assembled by a technician for operating use, instructions for use, etc. A kit may include a selection of test strips having one or more secondary redox couples. The kit may further include various other components for use with the test strips including control solutions for calibrating a meter, etc. The kits may also include instructions for using the test strips. These instructions may be printed on a substrate, such as paper or plastic, etc. As such, the instructions may be present in the kits as a package insert, in the labeling of the container of the kit or components thereof (i.e., associated with the packaging or sub-packaging) etc. In other embodiments, the instructions are present as an electronic storage data file present on a suitable computer readable storage medium, e.g., CD-ROM, diskette, etc. In yet other embodiments, the actual instructions are not present in the kit, but means for obtaining the instructions from a remote source, e.g., via the Internet, are provided. An example of this embodiment is a kit that includes a web address where the instructions can be viewed and/or from which the instructions can be downloaded. As with the instructions, this means for obtaining the instructions is recorded on suitable media.

As for other details of the present invention, such as other types of analytes which may measured with the subject techniques, these may be appreciated in connection with the above-referenced patents and publications as well as those generally known or appreciated by those with skill in the art. The same may hold true with respect to method-based aspects of the invention in terms of additional acts as commonly or logically employed.

The invention is not to be limited to that which is described or indicated as contemplated with respect to each variation of the invention. Various changes may be made to the invention described and equivalents (whether recited herein or not included for the sake of some brevity) may be substituted without departing from the true spirit and scope of the invention. Any number of the individual parts or subassemblies shown may be integrated in their design. Such changes or others may be undertaken or guided by the principles of design for assembly.

Also, it is contemplated that any optional feature of the inventive variations described may be set forth and claimed independently, or in combination with any one or more of the features described herein.

Where a range of values is provided, it is understood that every intervening value, between the upper and lower limit of that range and any other stated or intervening value in that stated range is encompassed within the invention.

Reference to a singular item, includes the possibility that there are plural of the same items present. More specifically, as used herein and in the appended claims, the singular forms "a," "an," "said," and "the" include plural referents unless the specifically stated otherwise. In other words, use of the articles allow for "at least one" of the subject item in the description above as well as the claims below. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Without the use of such exclusive terminology, the term "comprising" in the claims shall allow for the inclusion of any additional element—irrespective of whether a given number of elements are enumerated in the claim, or the addition of a feature could be regarded as transforming the nature of an element set forth in the claims. Stated otherwise, unless specifically defined herein, all technical and scientific terms used herein are to be given as broad a commonly understood meaning as possible while maintaining claim validity.

In all, the breadth of the present invention is not to be limited by the examples provided.

That which is claimed is:

1. A method of measuring the concentration of a target analyte within a biological sample, the method comprising:
    applying the biological sample to an electrochemical cell having a redox reagent system comprising a first redox couple and at least one secondary redox couple, wherein the first redox couple is selected to mediate the target analyte;
    applying a square wave excitation voltage across the electrochemical cell;
    measuring a response current of the electrochemical cell, wherein the response current has a primary peak associated with mediation of the target analyte and one or more secondary peaks associated with the mediation of at least one secondary redox couple; and
    determining the concentration of the target analyte within the biological sample based on the primary and secondary current peaks.

2. The method of claim 1, wherein determining the concentration of the target analyte comprises applying a correction factor to the value of the measurement from the primary peak based on the value of the measurement from the secondary peak.

3. The method of claim 2, wherein determining the concentration of the target analyte comprises compensating for the effect that hematocrit in a blood sample has on the value of the primary peak measurement.

4. The method of claim 2, wherein determining the concentration of the target analyte comprises compensating for the effect that the temperature of the biological sample has on the value of the primary peak measurement.

5. The method of claim 1, wherein the first redox couple comprises a mediator for the glucose reaction with a glucose specific enzyme, and at least one secondary redox couple comprises a redox couple that does not interfere with the primary glucose reaction or it's mediation.

6. The method of claim 1, wherein the square wave is superimposed over a potential step function to provide a potential waveform.

7. The method of claim 1, wherein the measuring a response current is performed within less than about 1 second.

8. The method of claim 1, wherein the square wave excitation voltage is applied at a frequency not less than about 100 Hz and scanned across range of about 1 volt.

9. The method of claim 1, wherein the target analyte is glucose and the biological sample is blood.

10. A system comprising:
    a test strip comprising an electrochemical cell having a redox reagent system comprising a first redox couple and at least one secondary redox couple, wherein the first redox couple is selected and configured to mediate the target analyte and provide a primary peak and the at least one secondary redox couple selected and configured so as to provide a secondary peak; and
    a meter configured for applying a square wave excitation voltage across the electrochemical cell and providing the primary peak and secondary peak, wherein the test strip is configured for electrical engagement with the meter.

11. The system of claim 10, wherein the target analyte is glucose.

12. The system of claim 10, wherein the target analyte is glucose and the secondary redox couple signal is used to compensate for hematocrit.

13. The system of claim 10, wherein the first redox couple comprises a glucose mediator and at least one secondary redox couple comprises a redox couple that does not interfere with the primary glucose reaction or it's mediation.

14. A device comprising:
    an electrochemical cell having a redox reagent system comprising a first redox couple and at least one secondary redox couple, wherein the first redox couple is selected and configured to mediate the target analyte and provide a primary peak and the at least one secondary redox couple selected and configured to provide a secondary peak; and
    a meter configured for applying a square wave excitation voltage across the electrochemical cell and providing the primary peak and the secondary peak, wherein the meter is in electrical communication with the electrochemical cell.

15. The device of claim 14, wherein the target analyte is glucose.

16. The device of claim 14, wherein the target analyte is glucose and the secondary redox couple signal is used to compensate for sample temperature.

17. The device of claim 14, wherein the first redox couple comprises a glucose mediator and at least one secondary redox couple comprises a redox couple that does not interfere with the primary glucose reaction or it's mediation.

* * * * *

UNITED STATES PATENT AND TRADEMARK OFFICE
CERTIFICATE OF CORRECTION

PATENT NO. : 7,699,973 B2  
APPLICATION NO. : 11/479544  
DATED : April 20, 2010  
INVENTOR(S) : Simon Tonks Page 1 of 1

It is certified that error appears in the above-identified patent and that said Letters Patent is hereby corrected as shown below:

Col. 10, line 7, claim 5, replace "it's" with "its".

Col. 10, line 40, claim 13, replace "it's" with "its".

Col. 10, line 62, claim 17, replace "it's" with "its".

Signed and Sealed this  
Fifth Day of April, 2011

David J. Kappos  
*Director of the United States Patent and Trademark Office*